United States Patent [19]

Li et al.

[11] Patent Number: 5,741,540
[45] Date of Patent: Apr. 21, 1998

[54] METHOD OF FORMING SOLID STATE HUMIDITY SENSOR

[75] Inventors: Yingjeng James Li, Pingtung; Ping Ping Tsai, Hsinchu, both of Taiwan

[73] Assignee: Industrial Technology Research Institute, Hsinchu, Taiwan

[21] Appl. No.: 587,168

[22] Filed: Jan. 16, 1996

[51] Int. Cl.$^6$ ....................................................... B05D 5/12
[52] U.S. Cl. ...................... 427/126.3; 101/483; 427/265; 427/314; 427/404; 427/419.2; 427/430.1
[58] Field of Search ...................... 101/483; 427/126.3, 427/265, 314, 404, 419.2, 430.1

[56] References Cited

U.S. PATENT DOCUMENTS

| | | | |
|---|---|---|---|
| 4,635,027 | 1/1987 | Miyoshi et al. | 338/34 |
| 5,001,453 | 3/1991 | Ikejiri et al. | 338/35 |

*Primary Examiner*—Bernard Pianalto
*Attorney, Agent, or Firm*—W. Wayne Liauh

[57] ABSTRACT

A method for forming a solid state humidity sensor is disclosed which comprises the steps of: (a) dissolving a tungstate salt into an aqueous solution; (b) adjusting the pH of the aqueous tungstate salt solution to below 8.5; (c) forming one or a pair of electrodes on an insulating substrate; (d) placing the substrate into the pH-adjusted aqueous tungstate salt solution and heating the aqueous solution containing the substrate at temperatures above 70° C. to thereby form a pyrochlore-type crystalline tungsten trioxide film over the electrode or pair of electrodes; and (e) forming another electrode over the pyrochlore-type crystalline tungsten trioxide film if only one electrode is formed during step (c). Alternatively, the pyrochlore-type crystalline tungsten trioxide film can be formed over or between the electrodes by heating the pH-adjusted aqueous tungstate salt solution to cause a precipitation of pyrochlore-type crystalline tungsten trioxide, then screen-printing the pyrochlore-type crystalline tungsten trioxide powder on one or both of the electrodes to thereby form a humidity sensing element. The pyrochlore-type crystalline tungsten trioxide is represented by the general formula of $(M_2O)_x WO_3 \cdot zH_2O$, in which M is a cation, x is about 0.5, and z, which is the amount of crystalline water contained in said crystal, is typically less than 2.

15 Claims, 9 Drawing Sheets

METHOD OF FORMING SOLID STATE HUMIDITY SENSOR

FIELD OF THE INVENTION

The present invention relates to a process for growing crystalline tungsten trioxide films of the pyrochlore-type. More specifically, the present invention relates to a process for growing pyrochlore-type crystalline tungsten trioxide films, which can be advantageously used as humidity sensing elements in solid state humidity sensors. The present invention also relates to resistance-type solid state humidity sensors made from these pyrochlore-type crystalline tungsten trioxide films.

BACKGROUND OF THE INVENTION

Typically, a humidity sensor measures the humidity level by measuring the change in the resistance of an element or the change in the electrostatic capacity of that element as it absorbs or releases moisture. Generally, humidity sensors can be classified as belonging to either one of two classes—a resistance type (or resistance-variation type) humidity sensor and a capacitance type (or capacitance-variation type) humidity sensor. A resistance type humidity sensor detects relative humidity by measuring the change in the resistance of an element corresponding to the ambient humidity. In comparison, a capacitance type humidity sensor detects humidity by measuring the change in the electrostatic capacity of an element corresponding to the ambient humidity. The capacitance type humidity sensors typically do not exhibit a satisfactory linear relationship between the capacitance and humidity, and an external circuit is required to overcome this disadvantage. This increases the manufacturing cost of capacitance-change type humidity sensors. Thus, the resistance type humidity sensors, which generally exhibit a linear relationship between the resistance and humidity, appear to have been the preferred choice.

Most of the resistance type humidity sensors include an electrolytic, polymeric, or metallic oxide sensor element. An electrolytic sensor element, which has become the most predominant type of humidity sensors, is made by forming a layer of moisture-lyzable (i.e., can be hydrolyzed by moisture) electrolyte on an insulating moisture-absorbing substrate. U.S. Pat. No. 4,635,027 discloses a resistance-variation type moisture sensor, which comprises a moisture sensitive film made of a moisture sensitive material coated on an insulating substrate, such as alumina or glass. The moisture sensitive material consists essentially of sodium styrenesulfonate, methylene-bis-acrylamide, polyvinyl alcohol, and polyethylene glycol. The polyethylene glycol is contained in the moisture sensitive film in an amount ranging from 3 to 7 parts by weight per 100 parts by weight of sodium styrenesulfonate.

U.S. Pat. No. 5,001,453 discloses a humidity sensor which includes an insulating substrate, a pair of electrodes formed on the insulating substrate, and a porous silica film with carbon particles dispersed therein formed over the insulating substrate and electrodes. A silica film can be formed over the porous silica film, either directly on the porous silica film containing the carbon particles, or directly on the insulating substrate with the electrodes formed thereon to increase adhesion between the porous silica film and the substrate.

The above mentioned humidity sensors involve moisture-absorbing materials, which, after long term usage in a high humidity environment, such as in certain high humidity applications or when used in high humidity areas such as South and Southwest Texas and Florida, will experience property degradation. Also, these materials are thermally unstable and will be subject to instant destruction when exposed to high temperature environments. Additionally, these materials also lack structural integrity and desired ruggedness.

In summary, most of the today's humidity sensors contain a humidity sensing element made from one of the following materials: (a) a moisture-lyzable film containing a electrically conductive material (such as carbon particles); (b) a moisture-absorbing film containing an electrolyte material (such as sodium chloride); and (c) a polymeric electrolyte film. Type (a) materials are known to exhibit the disadvantages of having relatively narrow ranges of measurable humidity changes, because their resistances vary significantly with humidity especially at high humidity environments, and their relatively low sensitivity at low humidity environments. Type (b) materials also have relatively narrow ranges of measurable humidity changes. In addition, type (b) materials are not suitable for long term use at high humidity environments, because the electrolytes contained therein can be diluted and lost due to excessive moisture absorption. Type (c) materials can experience permanent damage at elevated temperatures. However, this problem is also shared by types (a) and (b) materials. All of types (a), (b), and (c) materials will experience gradual property degradation at high humidity environments. Another problem experienced by these humidity sensors is that non-linearity or different slopes of linearity may be experienced at different ranges of relative humidities. This problem is illustrated in the sensor material disclosed in the '027 patent.

Because of their superior linearity between the measured resistance and relative humidity, metal oxides and ceramics may be advantageously used as the sensing material for making humidity sensors. Metal oxides also provide the advantages of having desired ruggedness, durability, improved temperature and chemical resistances, and their ability for long term use at high-humidity environments. Those metal oxides that may be used for this application include the porous $Ba_{0.5}Sr_{0.5}TiO_3$, $Li_5AlO_4$, $Li_5GaO_4$, $TiO_2$/$SnO_2$, $\beta$-$Fe_2O_3$, etc. When metal oxides are used as the humidity sensing material, their quality is determined not only by the material so chosen, but also by the manufacturing process, including the sintering process. Metal oxides provide a humidity-sensitive electrical conductivity based on the principle that hydrogen ions ($H^+$ or $H_3O^+$) are conducted in the porous structure of the solid state conductor, and the relative humidity value can be measured based on the change in resistance between two spaced apart electrodes as a result of the change in the humidity of the surrounding environment.

Since metal oxides offer many potential advantages as the sensing material for humidity sensors, it is desirable to explore potential candidates that can provide improved performance as well as reduced cost and reduced impact on the environment (both during manufacture and disposal after spent).

One of the possible candidates for use as humidity sensing materials is tungsten oxide, which has been known to exist in several structures including: cubic, hexagonal, orthorhombic, monoclinic, and triclinic crystalline structures, and non-crystalline structures. Among these various types of tungsten oxide, the cubic-structured tungsten trioxide, which has a crystalline structure similar to that of pyrochlore (and hence is called in the present invention "pyrochlore-type tungsten trioxide"), is the one with the most capacious structure (i.e., with the largest amounts of free space and three-dimensional interconnection of tunnels). The pyrochlore-type tungsten trioxide has a general formula of $(M_2O)_xWO_3.zH_2O$, where M is a cation, and z is the amount of crystalline water.

The pyrochlore-type tungsten trioxide, whose structure is shown in FIG. 1, has a large number of cavities and tunnels. These cavities and tunnels would facilitate the mass transport of cations therewithin, and allow the pyrochlore-type tungsten trioxide to provide useful applications in ionic exchange, as an ionic conductive material, and in reduction-oxidation type intercalation reactions. However, some of the undesirable characteristics of the pyrochlore-type tungsten trioxide caused it to be excluded from consideration as a candidate for making solid state humidity sensors. The main reason is that pyrochlore-type tungsten trioxide will be transformed into a different crystalline phase when it is heated to temperatures of about 350° C. or higher. Most of the coating processes for making metal oxide films involve heating the coating material to very high temperatures, typically in excess of 350° C., so as to cause it to vaporize and be deposited on the surface of the substrate. During this heating process, the pyrochlore-type crystalline structure of tungsten trioxide would have been destroyed, thus rendering it impossible for use as a sensing element in a humidity sensor.

SUMMARY OF THE INVENTION

The primary object of the present invention is to develop a solid state humidity sensor which contains pyrochlore-type tungsten trioxide in its sensing element. More specifically, the primary object of the present invention is to develop a hydrothermal process for making pyrochlore-type crystalline tungsten trioxide powders and/or growing pyrochlore-type crystalline tungsten trioxide films on a substrate, so as to enable a solid state humidity sensor to be made from pyrochlore-type tungsten trioxide. The pyrochlore-type tungsten trioxide based humidity sensors developed in the present invention exhibit excellent linearity between the resistance and relative humidity, and provide excellent ruggedness, durability, improved temperature and chemical resistances, as well as improved durability for long term use in high-humidity environments. The pyrochlore-type tungsten trioxide has a general formula of $(M_2O)_xWO_3.zH_2O$, where M is a cation, x is approximately equal to 0.5, and z, which is the amount of crystalline water, is less than about 2. The value of z can vary depending on the water vapor pressure of the surroundings.

In the process disclosed in the present invention, a tungstate salt (such as sodium tungstate, $Na_2WO_4.2H_2O$) is first dissolved into a solution. Then, the pH of the tungstate salt solution is adjusted to acidic or slightly basic (pH less than 8.5). After heating in a pressured vessel at temperatures above 70° C., pyrochlore-type tungsten trioxide is obtained. Depending on whether a powder is formed during the hydrothermal process (due to precipitation), and the construction of the sensing element, the pyrochlore-type tungsten trioxide based sensing elements can be prepared according to four basic embodiments. First, a pair of electrodes can be screen-printed on one surface of a ceramic insulating substrate, then a powdery pyrochlore-type tungsten trioxide is screen-printed over the electrodes. Second, after the pair of electrodes are screen-printed on the surface of a ceramic insulating substrate, a pyrochlore-type crystalline tungsten trioxide film can be caused to grow over the electrodes. Third, one of the pair of electrodes is screen-printed on one surface of a ceramic insulating substrate, then the powdery pyrochlore-type tungsten trioxide is screen-printed over this electrode, followed by screen-printing the other half of the pair of electrodes over the pyrochlore-type tungsten trioxide. Fourth, after one of the pair of electrodes is screen-printed on the surface of the ceramic insulating substrate, the pyrochlore-type crystalline tungsten trioxide film is grown over the electrode, followed by screen-printing the other half of the pair of electrodes over the pyrochlore-type tungsten trioxide.

The method for preparing the solid state humidity sensors disclosed in the present invention can be classified according to whether a powder or film of pyrochlore-type tungsten trioxide is formed during the manufacturing process. In the first and third embodiments, the hydrothermal conditions are such that a powdery pyrochlore-type tungsten trioxide is formed. This can be achieved by conducting the hydrothermal reaction at a relatively high pH and/or using a saturated salt solution during the ionic exchange step. In the second and fourth embodiments, the hydrothermal conditions are designed such that a pyrochlore-type tungsten trioxide film is formed on the substrate.

The method for preparing the solid state humidity sensors disclosed in the present invention can be classified according to how the pyrochlore-type tungsten trioxide layer is placed relative to the electrodes. In the first and second embodiments, the pyrochlore-type tungsten trioxide is formed over the pair of comb-shaped electrodes. In comparison, in the third and fourth embodiments, the pyrochlore-type tungsten trioxide is formed between the pair of electrodes.

In summary, the present invention discloses a process by which pyrochlore-type crystalline tungsten trioxide films can be formed on a substrate with a pair of printed electrodes, so as to enable a solid state humidity sensor to be made which contains a pyrochlore-type tungsten trioxide as the humidity sensing material. The pyrochlore-type tungsten trioxide based humidity sensors developed in the present invention exhibit excellent linearity between the resistance and relative humidity, excellent ruggedness and durability, improved temperature and chemical resistances, and improved durability for long term use at high-humidity environments.

The present invention also discloses a method for growing pyrochlore-type crystalline tungsten trioxide film which comprises the steps of: (a) dissolving a tungstate salt into an aqueous solution; (b) adjusting the pH of the aqueous tungstate salt solution to below 8.5; and (c) placing a substrate into the pH-adjusted aqueous tungstate salt solution and heating the solution at temperatures above 70° C. to thereby form a pyrochlore-type crystalline tungsten trioxide film on the substrate; (d) wherein the pH-adjusted aqueous tungstate salt solution contains at least 0.43M of the tungstate salt.

BRIEF DESCRIPTION OF THE DRAWING

The present invention will be described in detail with reference to the drawings showing the preferred embodiment of the present invention, wherein.

DETAILED DESCRIPTION OF THE PREFERRED EMBODIMENT

The present invention discloses a solid state humidity sensor which contains pyrochlore-type tungsten trioxide as its sensing element. The present invention allows a solid state humidity sensor to be made from pyrochlore-type tungsten trioxide by developing a novel process by which pyrochlore-type crystalline tungsten trioxide films can be grown over or between a pair of screen printed electrodes on an insulating substrate. The pyrochlore-type tungsten trioxide used in the present invention has a general formula of $(M_2O)_xWO_3 \cdot zH_2O$, where M is a small cation, such as $H^+$, $Li^+$, $Na^+$, $Ag^+$, or $NH_4^+$. Preferably, the value of x is approximately equal to 0.5, and z, which is the amount of crystalline water, is less than about 2. The value of z can vary depending on the water vapor pressure of the surroundings.

Figure 1:
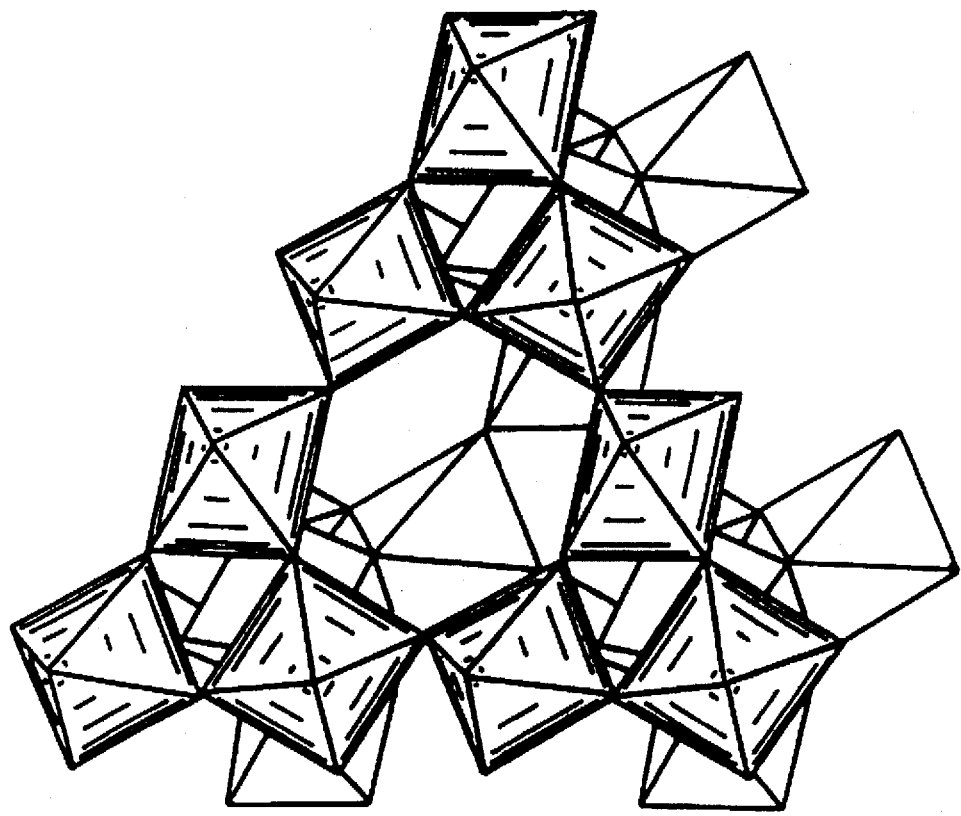
FIG. 1 is the crystalline structure of pyrochlore-type tungsten trioxide.

FIG. 1 shows a schematic drawing of the crystalline structure of pyrochlore-type tungsten trioxide. Conventionally, pyrochlore-type tungsten trioxide was not considered as a suitable candidate material for making solid state humidity sensors because the pyrochlore-type tungsten trioxide will be transformed into a different crystalline phase when it is heated to temperatures of about 350° C., and most of the film coating processes involve heating the coating material above this temperature. During this heating process, the pyrochlore-type crystalline structure of tungsten trioxide would have been destroyed, thus rendering it impossible for use as a sensing element in a humidity sensor. The present invention allows the pyrochlore-type crystalline structure of tungsten trioxide to be advantageously utilized as a solid state humidity sensing material.

Figure 4:
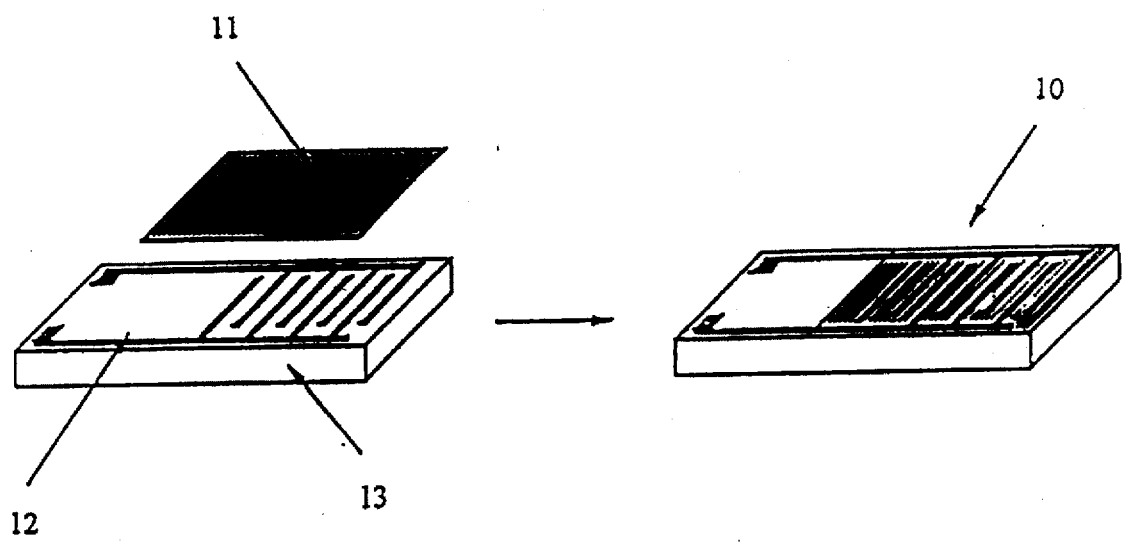
FIG. 4 is a schematic diagram of the steps of forming a humidity sensing element by screen-printing a pyrochlore-type tungsten trioxide over a pair of comb-shaped electrodes on an insulating substrate.

In the process disclosed in the present invention, a tungstate salt (such as sodium tungstate, $Na_2WO_4 \cdot 2H_2O$) is first dissolved into a solution. Then, the pH of the tungstate salt solution is adjusted to acidic or slightly basic (pH less than 8.5). After heating in a pressured vessel, the pyrochlore-type tungsten trioxide is obtained. The pyrochlore-type tungsten trioxide based sensing element can be prepared according to one of four basic embodiments. These embodiments can be categorized primarily based on whether a powdery, or a film of pyrochlore-type crystalline tungsten trioxide is formed. This can be controlled by, among other things, adjusting the pH of hydrothermal reaction by the concentration of the tungsten salt, or by the type of cation to be included in the crystalline structure. In the first embodiment, a pair of electrodes are screen-printed on one surface of a ceramic insulating substrate, then a powdery pyrochlore-type crystalline tungsten trioxide is screen-printed over the electrodes. FIG. 4 is a schematic diagram of the steps of forming a humidity sensing element by screen-printing a powdery pyrochlore-type tungsten trioxide layer 11 over a pair of comb-shaped electrodes 12 on an insulating substrate 13 according to this first embodiment.

Figure 5:
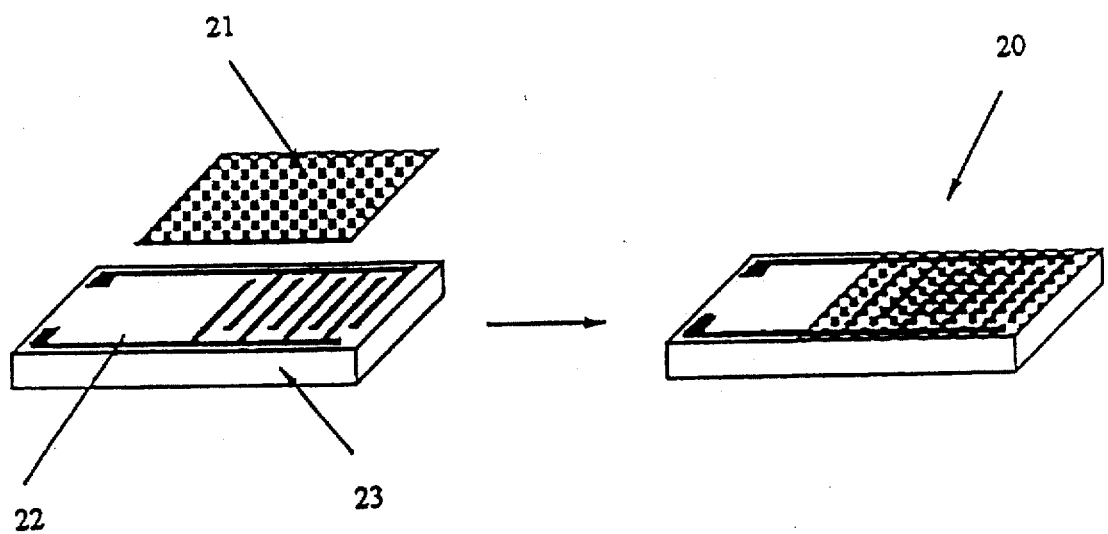
FIG. 5 is a schematic diagram of the steps of forming a humidity sensing element by growing a layer of crystalline pyrochlore-type tungsten trioxide over a pair of comb-shaped electrodes on an insulating substrate.

In the second embodiment of the present invention, after the pair of electrodes are screen-printed on the surface of a ceramic insulating substrate, a pyrochlore-type crystalline tungsten trioxide film is grown over the electrodes. FIG. 5 is a schematic diagram of the steps of forming a humidity sensing element 20 by growing a layer of the pyrochlore-type crystalline tungsten trioxide 21 over a pair of comb-shaped electrodes 22 on an insulating substrate 23, according to the second embodiment.

Figure 6:
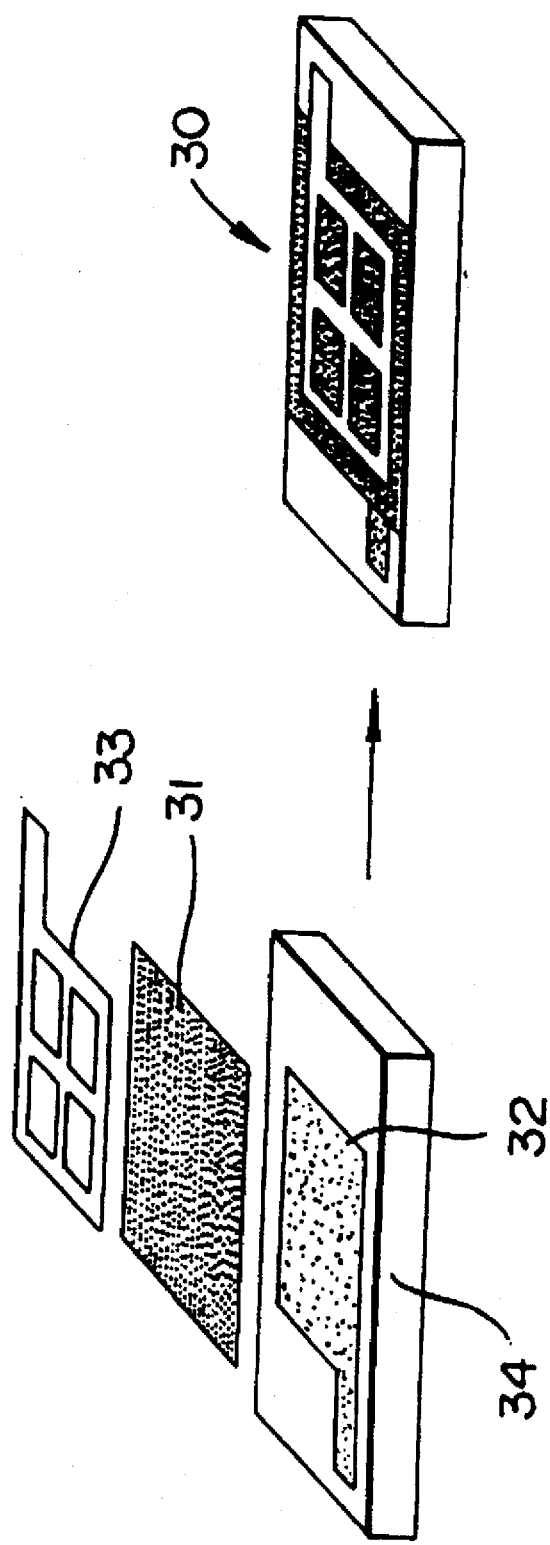
FIG. 6 is a schematic diagram of the steps of forming a humidity sensing element by screen-printing a pyrochlore-type tungsten trioxide between a pair of comb-shaped electrodes on an insulating substrate.

In the third embodiment, one of the pair of electrodes is screen-printed on one surface of a ceramic insulating substrate, then the powdery pyrochlore-type tungsten trioxide is screen-printed over this electrode, followed by screen-printing the other half of the pair of electrodes over the pyrochlore-type tungsten trioxide. FIG. 6 is a schematic diagram of the steps of forming a humidity sensing element 30 by forming, via screen-printing, a powdery pyrochlore-type tungsten trioxide layer 31 between a lower layer electrode 32 and an upper layer electrode 33, both are formed on an insulating substrate 34, according to the third embodiment.

Figure 7:
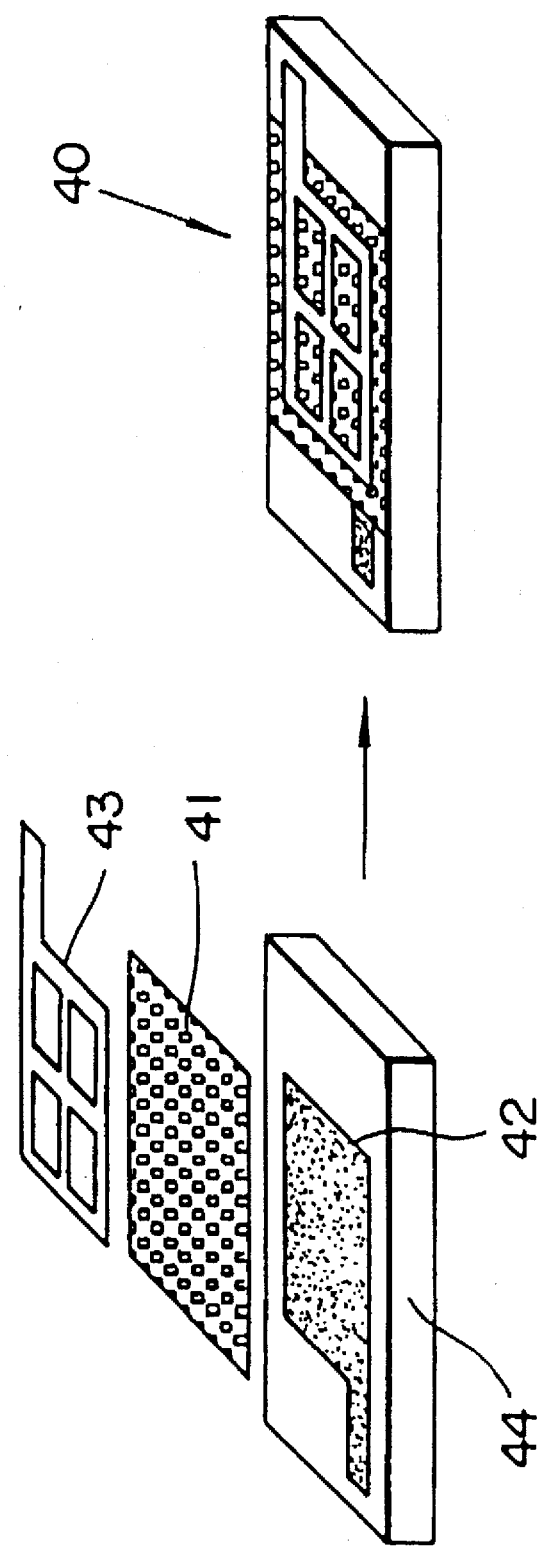
FIG. 7 is a schematic diagram of the steps of forming a humidity sensing element by growing a layer of crystalline pyrochlore-type tungsten trioxide between a pair of comb-shaped electrodes on an insulating substrate.
Figure 8:
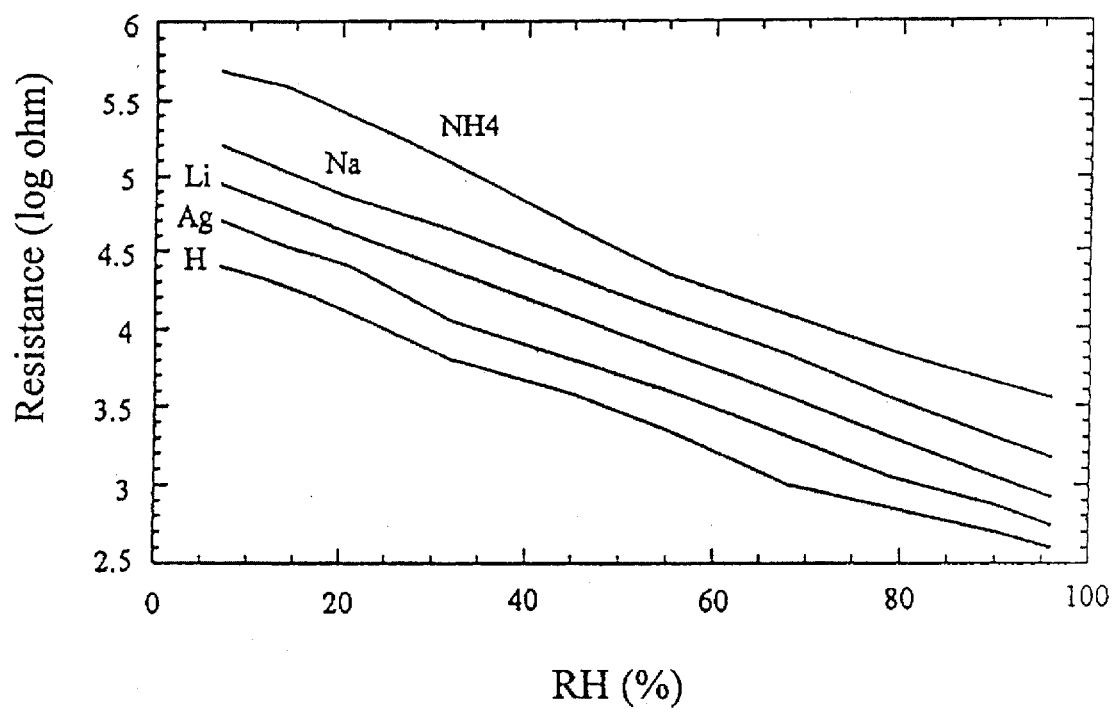
FIG. 8 shows plots of the relationships between the resistances and relative humidity measured from the humidity sensing elements made from the pyrochlore-type tungsten trioxides containing different cations.
Figure 9:
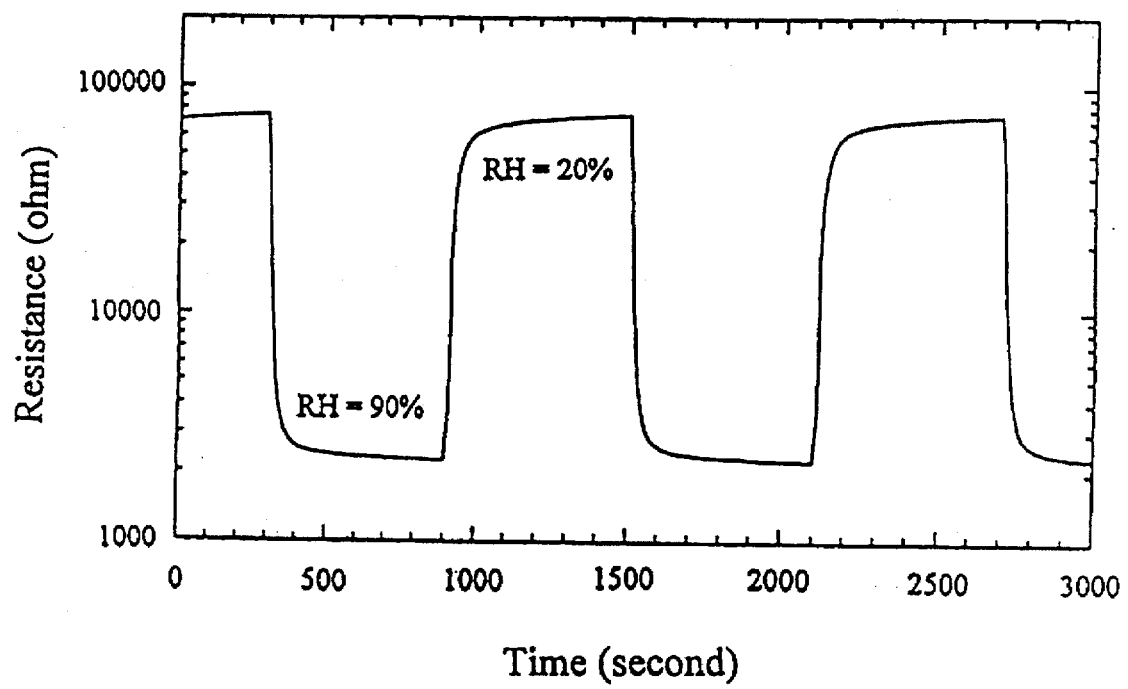
FIG. 9 shows a plot of resistance vs. time measured by a humidity sensing element made from the pyrochlore-type tungsten trioxide of the present invention to illustrate the excellent response speed during the humidity change.

In the fourth embodiment, after one of the pair of electrodes is screen-printed on the surface of the ceramic insulating substrate, the pyrochlore-type crystalline tungsten trioxide film is grown over the electrode, followed by screen-printing the other half of the pair of electrodes over the pyrochlore-type tungsten trioxide. In the third and fourth embodiments, the pyrochlore-type tungsten trioxide film is either screen-printed or grown between the pair of electrodes. FIG. 7 is a schematic diagram of the steps of forming a humidity sensing element 40 by growing a layer of crystalline pyrochlore-type tungsten trioxide 41 between the lower layer electrode 42 and the upper layer electrode 43 on an insulating substrate 44, according to the fourth embodiment.

Figure 2:
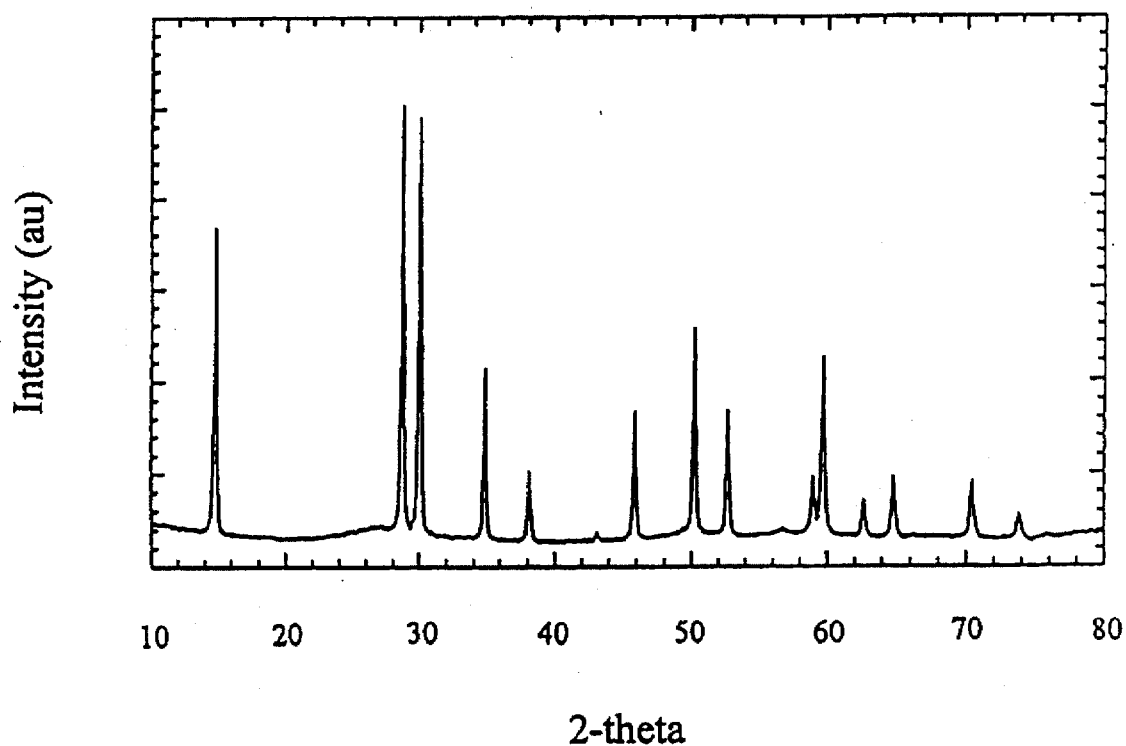
FIG. 2 is an X-ray diffraction chart of a powdery sodium form of the pyrochlore-type tungsten trioxide.
Figure 3:
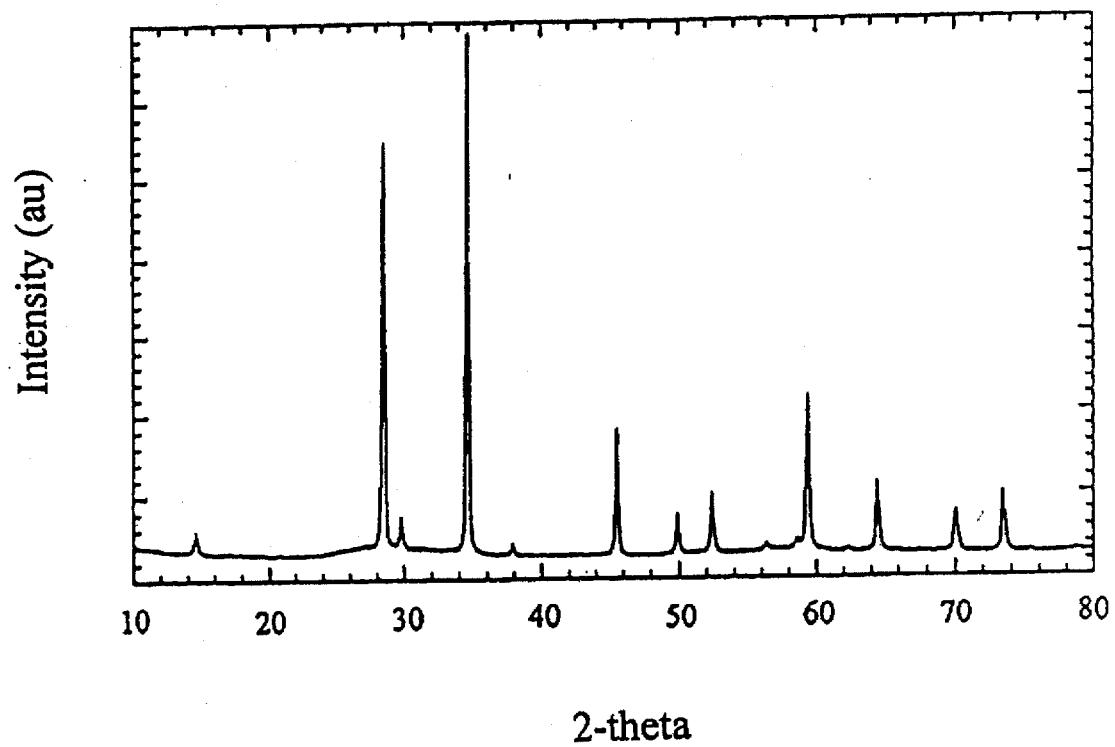
FIG. 3 is an X-ray diffraction chart of a crystalline film sodium form of the pyrochlore-type tungsten trioxide.

FIG. 2 is an X-ray diffraction chart of a powdery pyrochlore-type crystalline tungsten trioxide of the sodium form (i.e., containing sodium ions in the crystalline structure). And FIG. 3 is an X-ray diffraction chart measured from a pyrochlore-type crystalline tungsten trioxide film of the sodium form. It can be seen from FIGS. 2 and 3 that the powdery pyrochlore-type crystalline tungsten trioxide and the pyrochlore-type crystalline tungsten trioxide film exhibited the same phase with difference of orientation. As discussed earlier, the pyrochlore-type tungsten trioxide based humidity sensors developed in the present invention exhibit excellent linearity between the resistance and relative humidity, excellent ruggedness and durability, improved temperature and chemical resistances, and improved durability for long term use at high-humidity environments.

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EXAMPLE 1

De-ionized water was added to 25 g of sodium tungstate dihydrate ($Na_2WO_4 \cdot 2H_2O$, from Showa Chemicals, Inc., Japan) until the total volume thereof reached 50 ml. Then, concentrated hydrochloric acid was slowly added to the above prepared solution until the pH of the mixture reached 7.5. The mixture was introduced into a 125-ml non-corrosive pressure vessel (Parr 4748, Parr Instrument, Molin, Ill., USA). The vessel was heated in an oven at a temperature of 120° C. for 24 hours. After cooled to room temperature, the vessel was opened and a white powder, which was a pyrochlore-type tungsten trioxide of the sodium form (designated as Na-pyro-$WO_3$), was obtained. After being rinsed with de-ionized water several times, the white powder was soaked in a 1M nitric acid solution at 70° C. The nitric acid solution, in which the white powder was soaked, was renewed every three hours for five times. Then, a yellowish powder was obtained. The yellowish powder was rinsed with de-ionized water several times and then soaked at 70° C. in a saturated lithium carbonate solution, which was renewed every three hours for five times. The white powder so obtained was pyrochlore-type tungsten trioxide of the lithium form (designated as Li-pyro-$WO_3$). The pyrochlore-type tungsten trioxide of the lithium form was screen-printed over an insulation substrate containing a pair of comb-shaped electrodes, as shown in FIG. 4.

EXAMPLE 2

30 ml of ammonia water was gradually added to 15 g of tungstic acid ($H_2WO_4$), then concentrated hydrochloric acid was slowly added to the above prepared solution until the pH of the mixture reached 3.5. After filtration, the clear filtrate and an alumina substrate having one side thereof printed with a pair of comb-shaped electrodes were placed inside a 125-ml non-corrosive pressure vessel (Parr 4748, Parr Instrument, Molin, Ill., USA). The vessel was heated in an oven at a temperature of 150° C. for 24 hours. After cooled to room temperature, the vessel was opened and a humidity sensing element containing a layer of pyrochlore-type tungsten trioxide film (which was $NH_4$-pyro-$WO_3$) formed on the surface of the substrate, was obtained. The procedure in forming the pyrochlore-type tungsten trioxide film over the electrodes is summarized in FIG. 5.

EXAMPLE 3

De-ionized water was added to 25 g of sodium tungstate dihydrate ($Na_2WO_4 \cdot 2H_2O$) until the total volume thereof reached 50 ml. Then, concentrated hydrochloric acid was slowly added to the above prepared solution until the pH of the mixture reached 7.5. The mixture was introduced into a 125-ml non-corrosive pressure vessel (Parr 4748, Parr Instrument, Molin, Ill., USA). The vessel was heated in an oven at a temperature of 180° C. for 24 hours. After cooled to room temperature, the vessel was opened and a white powder, which was the sodium form of pyrochlore-type tungsten trioxide, was obtained. After being rinsed with de-ionized water several times, the white powder was soaked at 70° C. in a 1M silver nitrate solution, which was renewed every three hours for five times. The white powder so obtained was the silver form of pyrochlore-type tungsten trioxide (designated as Ag-pyro-$WO_3$). Following the procedure as described in FIG. 6, a layer of the silver form of pyrochlore-type tungsten trioxide film was screen-printed over an electrode on an insulation substrate. Then, a grid-shaped electrode was screen-printed over this silver form of pyrochlore-type tungsten trioxide film to obtain a humidity sensing element as shown in FIG. 6.

EXAMPLE 4

50 ml of concentrated hydrochloric acid was gradually added to 50 ml of saturated sodium tungstate dihydrate ($Na_2WO_4 \cdot 2H_2O$) solution, until the pH of the mixture reached 5.5. After filtration, the clear filtrate and an alumina substrate having one side thereof printed with an electrode were placed inside a 125-ml non-corrosive pressure vessel (Parr 4748, Parr Instrument, Molin, Ill., USA). The vessel was heated in an oven at a temperature of 120° C. for 24 hours. After cooled to room temperature, the vessel was opened and a humidity sensing element containing a layer of pyrochlore-type tungsten trioxide film formed over the electrode, was obtained. Thereafter, a grid-shaped electrode was screen-printed over the pyrochlore-type tungsten trioxide film. The procedure in forming the pyrochlore-type crystalline tungsten trioxide film between the electrodes is summarized in FIG. 7.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A method for growing pyrochlore-type crystalline tungsten trioxide film comprising the steps of:
   (a) dissolving a tungstate salt into an aqueous solution;
   (b) adjusting the pH of said aqueous tungstate salt solution to below 8.5; and
   (c) placing a substrate into said pH-adjusted aqueous tungstate salt solution and heating said aqueous solution containing said substrate at temperatures above 70° C. to thereby form a pyrochlore-type crystalline tungsten trioxide film on said substrate;
   (d) wherein said pyrochlore-type crystalline tungsten trioxide is represented by the general formula of $(M_2O)_x WO_3 \cdot zH_2O$, in which M is a cation, x is approximately equal to 0.5, and z is the amount of crystalline water contained in said crystal; and said pH-adjusted aqueous tungstate salt solution contains at least 0.43M of said tungstate salt.

2. A method for growing pyrochlore-type crystalline tungsten trioxide film according to claim 1 wherein said cation M is selected from the group consisting of $H^+$, $Li^+$, $Na^+$, $Ag^+$, and $NH_4^+$.

3. A method for growing pyrochlore-type crystalline tungsten trioxide film according to claim 1 which further comprising an ion exchange step by soaking said pyrochlore-type crystalline tungsten trioxide containing cation M in a second aqueous solution containing cation M', to thereby form a pyrochlore-type crystalline tungsten trioxide containing cation M'.

4. A method for growing pyrochlore-type crystalline tungsten trioxide film according to claim 1 wherein said aqueous solution containing said substrate is heated at temperatures above 120° C. during step (c).

5. A method for forming a solid state humidity sensor comprising the steps of:
   (a) dissolving a tungstate salt into an aqueous solution;

(b) adjusting the pH of said aqueous tungstate salt solution to below 8.5;

(c) forming one or a pair of electrodes on an insulating substrate;

(d) placing said substrate into said pH-adjusted aqueous tungstate salt solution and heating said aqueous solution containing said substrate at temperatures above 70° C. to thereby form a pyrochlore-type crystalline tungsten trioxide film over said electrode or pair of electrodes; and (e) forming another electrode over said pyrochlore-type crystalline tungsten trioxide film if only one said electrode is formed during step (c);

(f) wherein said pyrochlore-type crystalline tungsten trioxide is represented by the general formula of $(M_2O)_xWO_3 \cdot zH_2O$, in which M is a cation, x is approximately equal to 0.5, and z is the amount of crystalline water contained in said crystal; and said pH-adjusted aqueous tungstate salt solution contains at least 0.43M of said tungstate salt.

6. A method for forming a solid state humidity sensor according to claim 5 wherein said cation M is selected from the group consisting of $H^+$, $Li^+$, $Ag^+$, and $NH_4^+$.

7. A method for forming a solid state humidity sensor according to claim 5 which further comprising an ion exchange step by soaking said pyrochlore-type crystalline tungsten trioxide containing cation M in a second aqueous solution containing cation M', to thereby form a pyrochlore-type crystalline tungsten trioxide containing cation M'.

8. A method for forming a solid state humidity sensor according to claim 5 wherein said aqueous solution containing said substrate is heated at temperatures above 120° C. during step (d).

9. A method for forming a solid state humidity sensor according to claim 5 wherein said one or pair of electrodes are formed on said insulating substrate via a screen printing process.

10. A method for forming a solid state humidity sensor comprising the steps of:

(a) dissolving a tungstate salt into an aqueous solution;

(b) adjusting the pH of said aqueous tungstate salt solution to below 8.5;

(c) heating said pH-adjusted aqueous tungstate salt solution at temperatures above 70° C. to cause precipitation of a pyrochlore-type crystalline tungsten trioxide powder;

(d) forming one or a pair of electrodes on an insulating substrate; and (e) forming a layer of said pyrochlore-type crystalline tungsten trioxide over said electrode or pair of electrodes;

(f) forming another electrode over said pyrochlore-type crystalline tungsten trioxide film if only one said electrode is formed during step (d);

(g) wherein said pyrochlore-type crystalline tungsten trioxide is represented by the general formula of $(M_2O)_xWO_3 \cdot zH_2O$, in which M is a cation, x is approximately equal to 0.5, and z is the amount of crystalline water contained in said crystal; and said pH-adjusted aqueous tungstate salt solution contains at least 0.43M of said tungstate salt.

11. A method for forming a solid state humidity sensor according to claim 10 wherein said cation M is selected from the group consisting of $H^+$, $Li^+$, $Na^+$, $Ag^{3O}$, and $NH_4^+$.

12. A method for forming a solid state humidity sensor according to claim 10 which further comprising an ion exchange step of soaking said pyrochlore-type crystalline tungsten trioxide containing cation M in a second aqueous solution containing a second cation M', to thereby form a pyrochlore-type crystalline tungsten trioxide containing said second cation M'.

13. A method for forming a solid state humidity sensor according to claim 10 wherein said aqueous solution containing said substrate is heated at temperatures above 120° C. during step (c).

14. A method for forming a solid state humidity sensor according to claim 10 wherein said one or pair of electrodes are formed on said insulating substrate via a screen printing process.

15. A method for forming a solid state humidity sensor according to claim 10 wherein said layer of said pyrochlore-type crystalline tungsten trioxide is formed over said electrode or pair of electrodes via a screen printing process.

\* \* \* \* \*